United States Patent [19]

Lawson

[11] 4,276,139

[45] Jun. 30, 1981

[54] PROCESS FOR MAGNETIC SEPARATION AND COLLECTION OF VIABLE FEMALE AND MALE SPERMATOZOA

[76] Inventor: Rommon L. Lawson, 7905 Bangor Ave., Lubbock, Tex. 79424

[21] Appl. No.: 83,173

[22] Filed: Oct. 9, 1979

Related U.S. Application Data

[63] Continuation-in-part of Ser. No. 933,988, Aug. 16, 1978, Pat. No. 4,225,405, which is a continuation-in-part of Ser. No. 805,869, Jun. 13, 1977, abandoned.

[51] Int. Cl.³ ............................................ G01N 27/26
[52] U.S. Cl. .............................. 204/180 R; 23/230 B; 204/DIG. 5
[58] Field of Search .................. 204/180 R, 184, 185, 204/186, DIG. 9, DIG. 5; 424/12; 23/230 B

[56] References Cited

U.S. PATENT DOCUMENTS

| | | | |
|---|---|---|---|
| 3,649,499 | 3/1972 | Virtanen et al. | 204/180 R |
| 3,664,939 | 5/1972 | Luner et al. | 204/180 R |
| 4,155,831 | 5/1979 | Bhattacharya | 204/180 R X |
| 4,181,589 | 1/1980 | Brooks | 204/180 R |

Primary Examiner—G. L. Kaplan
Attorney, Agent, or Firm—Harvey B. Jacobson

[57] ABSTRACT

A process for separating and collecting viable female spermatozoa (X-chromosome) and male spermatozoa (Y-chromosome) comprises subjecting a semen sample to an electromagnetic field to cause the female and male spermatozoa to migrate in opposite directions along the direction of the magnetic field. The semen sample is placed in an elongated tube having closed ends and the tube aligned in the direction of the magnetic field whereby the female spermatozoa are collected at the end of the tube in which the magnetic flux of the magnetic field enters and the male spermatozoa are collected at the opposite end of the tube at which the magnetic flux exits.

12 Claims, 6 Drawing Figures

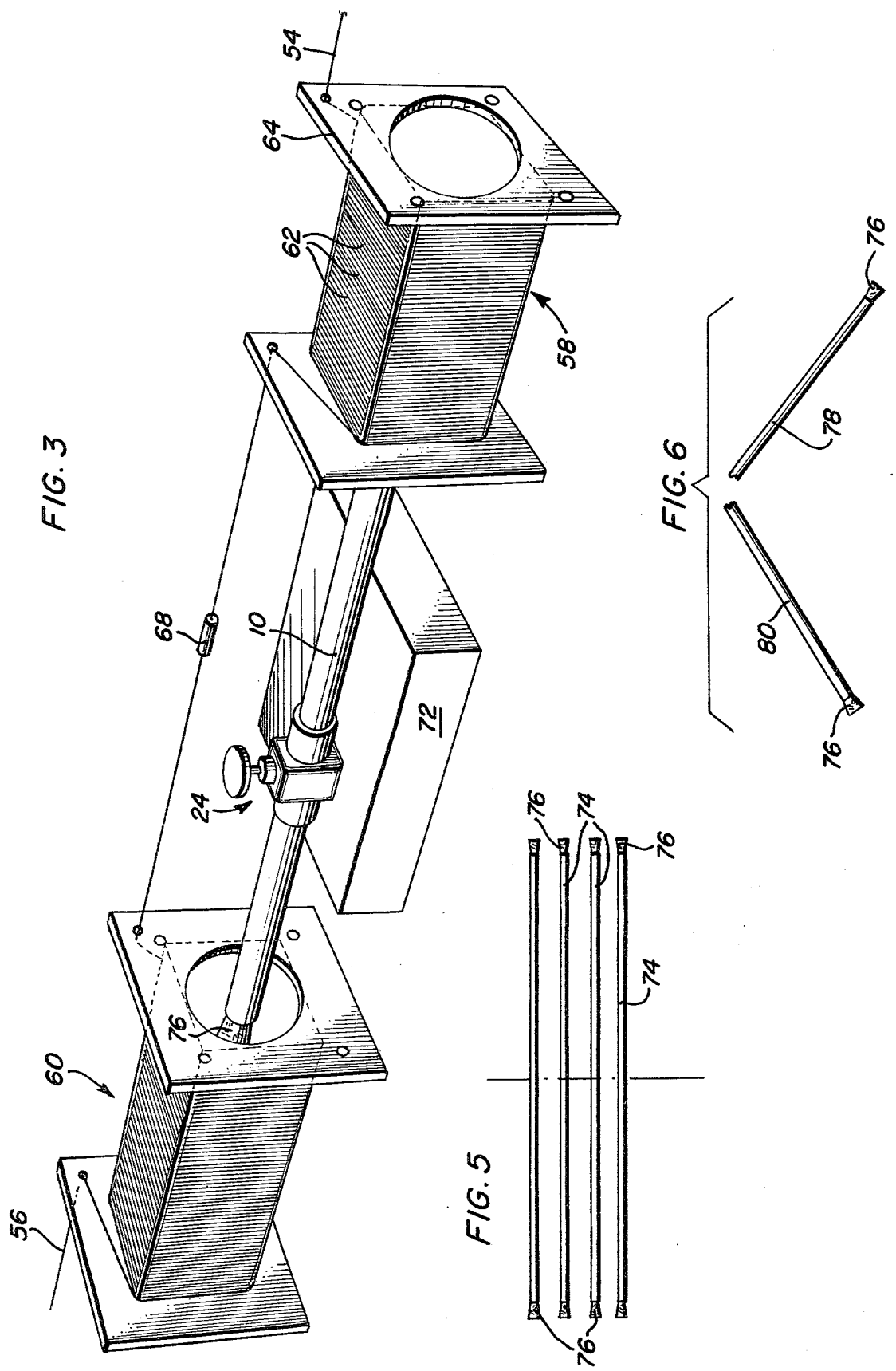

PROCESS FOR MAGNETIC SEPARATION AND COLLECTION OF VIABLE FEMALE AND MALE SPERMATOZOA

CROSS-REFERENCE TO RELATED APPLICATION

This application is a continuation-in-part of co-pending U.S. application Ser. No. 933,988, filed Aug. 16, 1978, now U.S. Pat. No. 4,225,405, which is a continuation-in-part of U.S. application Ser. No. 805,869, filed June 13, 1977, now abandoned.

BACKGROUND OF THE INVENTION

1. Field of the Invention

A workable process for separating and collecting viable female spermatozoa (X-chromosome) and male spermatozoa (Y-chromosome) would be of great value to the beef and dairy cattle industry by giving a higher percentage male or female offspring, depending on demand. The separation of male and female components of semen samples would enhance the probability of obtaining one sex over the other through an artificial insemination program by utilizing the proper semen fraction.

Accordingly, it is desirable to have a process for separating and collecting viable female spermatozoa and male spermatozoa.

2. Disclosure Statement

Sex differentiations between the male and female of mammalian species are very great and are far too extensive to explain by single gene transmission. In most higher animals, there are two separate sexes and they have various degrees of differentiation of body parts. Involved in a great majority of forms of life that have separate sexes are the chromosomes. Since the XY method is the most common method of sex determination, we will briefly say that within certain species there are pairs of autosomes and one pair of X-chromosomes in the female diploid cells, and pairs of autosomes and the paired X- and Y- chromosomes in the male.

In oogenesis the chromosomes pair and the eggs and polar bodies all receive the same kind of chromosomes—autosomes and one X- chromosome. In spermatogenesis, one pair of chromosomes is unlike and half of the sperm receive the X- chromosome while the other half receives the Y-chromosome. Sex determination depends upon which of the two types of sperm fertilizes the egg. Thus, we think of spermatozoa carrying the X- chromosome as being female-determining while those carrying the Y- chromosome are male-determining. Segregation of the XY pair and random fertilization explains superficially why some individuals develop into females and some into males. This is basically why in almost all mammalian species, about half of the members of each population are males and half are females. Thus, the chromatin difference in the spermatozoa allows one to separate the X- from the Y- types of sperm, thereby being able to control the sex of the offspring at the time of fertilization.

The determination of sex occurs at the time of fertilization depending on whether the ovum is fertilized by an X- or Y- chromatin spermatozoa. The X-spermatozoa, uniting with the egg (ova) yields a female and the Y-spermatozoa, a male. The female ovum is always the X-bearing chromatin material. In most mammalian species the union of the two haploid germ cells, the ovum X- with spermatozoa X- or Y-, the XX combination yields females and the XY combination yields males.

The introduction of artificial insemination as the preferential method of insemination in cattle emphasized the importance of selecting bull donors with regard to both their genetic quality and their fertilizing capacity. Also, the longtime hope of sex control was revived because of the feasibility of treating semen prior to use in order to increase the incidence of desired sex.

The desire of man to be able to predetermine sex before conception and thus alter the natural sex ratio has prompted many investigations to seek methods of separating out two populations of sperm.

In the literature, no appreciable contributions have been discovered towards this problem. The following items cited in Table I are related to this effort.

TABLE I

Prior Art Citations

| No. | Citation |
|---|---|
| 1. | ANNON. Aug. 22, 1949. Boy or Girl. Newsweek 34:44. |
| 2. | BERNSTEIN, MARIANNE E. 1949. A son for every family? Science Digest 25:43. |
| 3. | LUSH, J. L. 1925. The possibility of sex control by artificial insemination with centrifuged spermatozoa. J. Agric. Research 38:898–913. |
| 4. | HARVEY, E. NEWTON. 1946. Can the sex of mammalian offspring be controlled? J. of Heredity 37:71. |
| 5. | LINDAHL, PER ERIC. 1956. Counter-streaming centrifugation of bull spermatozoa. Nature 178:491–492. |
| 6. | LINDAHL, PER ERIC, and KIHLSTROM, J. E. 1952. Alterations in specific gravity during the ripening of bull spermatozoa. J. Dairy Sol. 35:393–401. |
| 7. | LINDAHL, PER ERIC. 1959. Separation of bull spermatozoa carrying X- and Y- chromosomes by counter streaming centrifugation. Animal Breeding Abstracts 27:758. |
| 8. | LINDAHL, PER ERIC. 1952. On the relationship between fertility and light-refracting power in bull spermatozoa. J. of Agric. Sci. 42. |
| 9. | ROBERTS, E. 1940. The effect of lactic acid and sodium bicarbonate on the sex ratio. J. of Heredity 31:499–500. |
| 10. | WOLFF, ARTHUR. 1941. Sex control in mammals. Michigan St. Coll. Vet. 1(2):53–54. |
| 11. | COLE, LEON J., et al. 1940. A test of sex control by modification of the acid-alkaline balance. J. of Heredity 31:501–502. |
| 12. | COLE, L. J., et al. 1933. Sex control again. J. of Heredity 24:265–274. |
| 13. | QUISENBERRY, J. H. 1945. Additional data on sex control in rabbits. |

TABLE I-continued
Prior Art Citations

| No. | Citation |
|---|---|
| | J. of Heredity 36:160. |
| 14. | QUISENBERRY, J. H. and CHANDIRAMANI, S. V. 1940. An experimental attempt to modify the sex ratio. J. of Heredity 31:503–505. |
| 15. | McPHEE, H. C. and EATON, O. N. 1942. Experimental attempts to modify the sex ratio. J. of Heredity 33:429–433. |
| 16. | CASIDA, L. E. and MURPHREE, R. L. 1942. Fertility and sex ratios in the rabbit from semen treated in vitro with lactic acid and sodium bicarbonate. J. of Heredity 33:434–438. |
| 17. | WEIR, J. A. 1953. Association of blood pH with sex ratio in mice. J. of Heredity 44:133–138. |
| 18. | WEIR, J. A. 1955. Male influence on the sex ratio of offspring in high and low blood pH. J. of Heredity 46:277–283. |
| 19. | WEIR, J. A. 1953. Influence of the male on sex ratio of offspring in high and low blood pH lines of mice. Genetics 38:700–701. |
| 20. | PEARL, RAYMOND, et al. 1913. Data on sex determination in cattle. Biol. Bull. 24:205–225. |
| 21. | McWHIRTER, K. G. 1956. Control of sex ratio in mammals. Nature 178: 870–871. |
| 22. | SHETTLES, L. B. 1960. Nuclear morphology of human spermatozoa. Nature 186:648–649. |
| 23. | SHETTLES, L. B. 1960. Biology: X and Y spermatozoa. Nature 187: 254–255. |
| 24. | SHETTLES, L. B. 1960. Nuclear structure of human spermatozoa. Nature 188:918–919. |
| 25. | SHETTLES, L. B. 1961. Human spermatozoa shape in relation to sex ratios. Fertility and Sterility 12:502–508. |
| 26. | SHETTLES, L. B. 1961. Human spermatozoa types. Gynaecologia 162: 154–162. |
| 27. | SHETTLES, L. B. 1961. Sperm morphology and sex ratios. J. of Urology 86:450–455. |
| 28. | SHETTLES, L. B. 1961. Conception and birth sex ratios. Obstet. and Gynecol. 18:122–130. |
| 29. | LUDWIG, WILHELM 1947. Uber Certation and spermiendimorphismus bei tier und mnsch. Zeitscher. Naturforsch. 2b(5/6):222–226. |
| 30. | HARTMAN, CARL G. 1957. How do sperms get into the uterus? Fertility and Sterility 8:403–427. |
| 31. | R-PHYSIOLOGISTS. Personal communication. |
| 32. | DUIJN, C. VAN 1960. Nuclear structure of human spermatozoa. Nature 188:916–918. |
| 33. | ROTHSCHILD. LORD. 1960. Biology: X and Y spermatozoa. Nature 253–254. |
| 34. | SHRODER, VERA N. 1933. Artificial control of sex in the progeny of mammals. Nature 131:329. |
| 35. | SHRODER, VERA N. 1932. Die physikalisch-chemische analyse einiger fragen der spermien-physiologie. Biol. Zhur. 1:24–29. |
| 36. | SHRODER, VERA N. 1934. Uber ionequilibrierte verdunnungslosungen fur die pferdespermien. Biol. Zhur. 3:465–476. |
| 37. | SHRODER, VERA N. 1941. Kunstliche geschlects-regulation der nachkommenschaft der saugetiere und ihre biologishe kontrolle. Zeitschr. fur Tierzuchtung und Zuchtungsbiol. 50:1–15. |
| 38. | SHRODER, VERA N. 1941. Uber die biochemischen und physiologischen eigentumlichkeiten der X- and Y- spermien. Zeitschr. fur Teirzuchtung und Zuchtungsbiol. 50:16–23. |
| 39. | MACHOWKA, W. W. and SCHEGALOFF, S. B. 1935. Die reaktion der spermatozoen auf konstanten strom (galvanotaxis). Archiv. fur Entwicklungsmechanik der Organismen. 133:694–700. |
| 40. | KORDTS, E. 1952. Untersuchungen uber die eignug der elektrophorese zur trennung der mannchen und weilchenbestimmenden spermien biem kaninchen. Zeitschr. fur Tierzuchtung und zuchtungsbiol. 60:221–240. |
| 41. | PILZ, A. 1952. Das verhalten der saugetiersspermien in elektrischen feld. Zietschr. fur Tierzuchtung und Zuchtungsbiol. 60:315–330. |
| 42. | GORDON, MANUEL J. 1957. Control of sex ratio in rabbits by electrophoresis of spermatozoa. Proc. Natnl. Acad. Sci. 95:913–918. |
| 43. | GORDON, MANUEL J. 1958. The control of sex. Sci. Amer. 199:87–94. |
| 44. | LEWIN, SHERRY 1956. Artificial sex regulation of mammalian offspring. Brit. Vet. J. 112:549–550. |
| 45. | MacPHERSON, J. W. and VESSELINOVITCH, S. D. 1959. Electrophoresis of bovine semen. Can. J. of Comp. Med. and Vet Sci. 23:375–376. |
| 46. | VESSELINOVITCH, S. D. and MacPHERSON, J. W. 1959. Electrophoresis of bovine spermatozoa. The Cornell Vet. 49:359–373. |
| 47. | VESSELINOVITCH, S. D. 1959. Microelectrophoresis of bovine spermatozoa. Can. J. of Comp. Med. and Vet. Sci. 23:1–19. |
| 48. | VESSELINOVITCH, S. D. 1960. Electrophoresis of spermatozoa and sex control. Cornell Vet. 50:326–330. |
| 49. | DIASIO, R. and GLASS, R. 1971. Effects of pH on the migration of X and Y sperm. Fertility and Sterility 22:5. |
| 50. | EMMERICH, E. and STOLKOWSKI, J. 1970. Influence of Mineral nutrition on sex distribution in the cow: prospective and experimental investigations. Enn. Endoc. (Paris) T. 31:2. |
| 51. | MORGAN, D. and ROAN, C. 1972. Nature 238:233. |

TABLE I-continued

Prior Art Citations

| No. | Citation |
|---|---|
| 52. | SEVING, A. 1968. Experiments on sex control by electrophoretic separation of spermatozoa in the rabbit. J. Reprod. Fer. 16:7-14. |

There are records of Greek physicians in 500 B.C. advising their patients, expectant mothers, to lie on their right side while sleeping and they would surely bear a son. If they slept on their left sides, they will give birth of a daughter (see Citation No. 1 in Table I).

It was not until after the Nobel Prize winning discovery of the sex-determining X- and Y- chromosomes by Professor T. H. Morgan in 1912 (see Citation No. 2 Table I) that any scientifically based theories were propounded on the control of the sex of the offspring. The majority of these theories are founded on the concept that the main differences between the spermatozoa which carry the larger X-chromosome (female producing) and the spermatozoa which carry the smaller Y-chromosome (male producing) are: weight, size, speed of locomotion, viability at various pH values, and overall electric charge.

In 1925, Lush (see Citation No. 3 in Table I) made many attempts to control the sex in rabbits by separating spermatozoa according to size by partial centrifugation and inseminating the fractions in females. He believed that there was dimorphism between the two types of spermatozoa, but stated that the observable difference as seen through the microscope was very small. The results of his work show that there was no significant deviation from the expected ratio of males to females in the offspring.

Harvey (see Citation No. 4 in Table I) in 1946 modified Lush's procedure. He believed that the size of the spermatozoa were all the same but that the X-chromosome-carrying spermatozoa would be more dense than the Y-chromosome-carrying spermatozoa due to the mass difference of the two chromosomes. If this were true, then a solution could be prepared which would intermediate in density between the two types of spermatozoa at a given temperature. By centrifugation the less dense Y spermatozoa would float while the more dense X spermatozoa would sink. Although Harvey did not test his theory by insemination, he calculated that the difference in the two types of spermatozoa is of the order of 2 in 10,000, a separation comparable to the separation of Uranium 235 from Uranium 238.

Lindahl (see Citation No. 5 in Table I) in 1956 applied the theory of separation of spermatozoa to cattle using the counter-streaming centrifuge. In this process, he collected the heavier spermotozoa (theoretically those with the X-chromosome) and inseminated them. This did not result in any significant divergence from the normal sex ratio. He cited Lindahl and Kihlstrom (see Citation No. 6 in Table I) as stating ". . . the density of bull spermatozoa increases in the course of their physiological maturation. This change in density is of such an order of magnitude that it totally obscures the difference in sedimentation rate due possibly to the difference in volume between the sex chromosomes." It could be possible that, in general, the X-carrying spermatozoa are usually larger and heavier than the Y-carrying spermatozoa, if there is no consistent amount of cytoplasm retained by the spermatozoa in maturation, or if there is no change in size as the age of the spermatozoon increases. If the amount of cytoplasm retained by the spermatozoon is inconsistent, then the relative differences in the masses of the sex chromosomes might not be sufficient to render the two types of spermatozoa separable by these methods. The above experiments, within their limits, seem to say that there is no correlation between the weight, size, or density of the spermatozoa and the type of sex chromosome it carries.

In 1959 Lindahl (see Citation No. 7 in Table I), using the counter streaming centrifugation method, produced a "heavy" and "light" sperm. The "heavy" and the "light" spermatozoa were used for the insemination of 142 and 121 cows, respectively. The difference between the two groups as regards fertility and sex ration was not statistically significant, but, within each group, higher fertility was significantly associated with a greater proportion of female calves born and, in the first group, with a lower centrifuge speed. Counter-streaming centrifugation of bull semen was carried out at velocities of 100-200 rpm. The results indicate that female determining spermatozoa are more liable to damage during centrifugation than are male determining spermatozoa. Fertility decreased more at the higher than at the lower velocities.

Lindahl (see Citation No. 8 in Table I) in 1952 also reports that the specific gravity of bull spermatozoa increases during ripening of the cells. This process is most pronounced at maturation due to loss of residual protoplasm, but continues also later and seems to form part of the changes underlying "over-ripening". The rise in density probably depends upon loss of water accompanied by a corresponding decrease in volume. However, the water still present is extremely firmly bound and resists high osmotic pressures (186 atmospheres). The ripe spermatozoa include a series of ripening stages, one of which represents the maximal fertile state.

In 1940 Roberts (see Citation No. 9 in Table I) douched the vagina of female rats with weak solutions of lactic acid or sodium bicarbonate less than two hours before mating. In the cases in which he used lactic acid he found that in 103 litters there were 280 males and 467 females. When he used sodium bicarbonate he found that in 104 litters there were 420 males and only 200 females. This would indicate that variation of vaginal pH could influence the ratio of the sexes of the offspring. Roberts offered no theories to explain his results, but it would appear that the pH in the vagina affected either the survival time of one of the two types of spermatozoa or affected the fertility of one type of spermatozoa.

Wolff (see Citation No. 10 in Table I) found in 1941 that the pH of the vagina at fertilization altered the normal sex ratio of the offspring. He reported that bicarbonate ions would produce more male while lactic acid would produce more female offspring, which is in agreement with Roberts (see Citation No. 9 in Table I).

At this time Cole, et al. (see Citation Nos. 11 and 12 in Table I) were performing this experiment with both rats and rabbits. Using lactic acid douches they found that in rats 447 males were produced to 408 females. When sodium bicarbonate was used 452 males and 439 females resulted, almost a 1:1 sex ratio in both instances. Fewer rabbits were obtained, but their sex ratio was almost 1:1 in each case. They went a step further by inseminating female rabbits with semen treated with either a weak acid or base, but only negative results were obtained.

Quisenberry (see Citation No. 13 in Table I) and Quisenberry and Chandiramani (see Citation No. 14 in Table I) were working on this problem in 1940 and found no significant divergence from the expected sex ratio when they used the vaginal douche technique in rats and rabbits.

McPhee and Eaton (see Citation No. 15 in Table I) working with rabbits and swine in 1942 failed to find any significant modification of the normal sex ratio as a result of acid or alkali douche treatments in 2,383 rabbit offspring and 219 swine offspring. Casida and Murphree (see Citation No. 16 in Table I) in 1942 found no change in the expected sex ratio of the offspring of rabbits when vaginal doubhes of various pH value were administered prior to fertilization.

Although Roberts and Wolff (see Citations No. 9 and 10, respectively, in Table I) did meet with success in their work with vaginal douches in the control of sex of the offspring, many others did not.

Weir (see Citations 17, 18 and 19 in Table I) began in 1953 a new series of experiments in which he developed two strains of mice, one with an average blood pH of 7.42 and the other with an average blood pH of 7.46. He found that the interbreeding of those mice with the blood pH of 7.42 altered the female/male sex ratio from 50:50 to 60:40 and the interbreeding of the mice with the blood pH of 7.46 altered the ratio of about 40:60. By cross breeding or reciprocal mating of different sexes of the two strains, he demonstrated that it was the blood pH of the male and not the female which determined the sex ratio of the young. Weir theorized that ". . . The association of an excess of females with low blood pH suggests that the genetic constitution of the mother may set up chemical conditions which in turn may act on the spermatozoa of the father to favor or handicap either the X or Y type, making for differential sex ratios in the resulting litters."

McWhirter (see Citation No. 21 in Table I) in 1956 tried to determine whether Weir's idea could be applied to other mammals and whether the blood pH changes which occur or which could be developed by selective breeding could affect the sex ratio of the offspring. He came to believe that significant variation of the sex ratio could be accomplished in other animals if a selected sire with the appropriate blood pH was used to father the offspring. The major objection to this method is that only certain males could be used if a particular sex offspring were desired.

Pearl, et al. (see Citation No. 20 in Table I) proposed in 1913 a method in which the time of copulation or insemination was varied with respect to the time of ovulation or period of "heat". They observed that when copulation in cattle took place during early heat, 31 males and 51 females were conceived and born. When copulation took place in late heat, 42 males and only 34 females were produced. They summarized: "As the time of coitus approaches the end of the oestrous period, there is a progressive increase in the proportion of male young born."

Shettles (see Citations 22 through 28 in Table I) in 1960 and 1961 has made some startling discoveries which seem to support this theory. Using a phase contrast microscope for observation of human spermatozoa he found two distinct populations of spermatozoa with regard to head and nuclear size and shape. One population was larger and had ovoid heads with a nucleus of similar shape. These were fewer in number than the other population which was smaller and had a round head containing a round nucleus. He theorized the larger spermatozoa were those containing the larger X-chromosome and would therefore produce female progeny while the smaller spermatozoa were those containing the X-chromosome and would produce male offspring. He went a step further in an attempt to explain the time factor of fertilization and its effect on the sex ratio. He theorized that the Y-spermatozoa were smaller than the X-spermatozoa, and they could swim faster. If insemination were immediately before ovulation, the Y-spermatozoa would reach the egg first and the resulting zygote would be male. (Ludwig (see Citation No. 29 in Table I) agrees with this theory). If insemination were some time prior to ovulation, then the weaker Y-spermatozoa would not be able to survive the conditions in the female reproductive tract as well as the X-spermatozoa and would be fewer in number. Therefore, at fertilization the probability that the zygote would be female would be much higher.

According to Hartman (see Citation No. 30 in Table I) the major role in the migration of spermatozoa in humans to the site of fertilization is played by muscular contraction of the walls of the female reproductive tract. He states that sexual stimulation through neural pathways causes an output of oxytocin which increases the muscular activity of the genital tract of the female. He further states that the main function of the tail of the spermatozoa is to effect the penetration of the corona radiata cells of the ovum itself. Some reproduction physiologists (See Citation No. 31 in Table I) are in agreement that the swimming of the sperm in the female reproductive tract could be compared to a man trying to swim in a hurricane. The massive movements of the ocean (fluid in uterus and oviducts) would be much greater than the feeble swimming of man (spermatozoa). If one holds to the latter beliefs, then he could not say that the Y-spermatozoa swim faster and reach the egg first.

Other points of conflict with Shettles' work have been raised by C. van Duijn and Rothschild (see Citation Nos. 32 and 33, respectively, in Table I). Rothschild states that there is so far no evidence that physical differences have been found between the X- and Y-spermatozoa, using phase contrast microscopy. C. van Duijn believes that Shettles is seeing artifacts due to a maladjusted optical element in his phase contrast microscope.

Vera N. Shroder (sometimes spelled Shreder) (see Citation Nos. 34 and 35 in Table I) in 1932 studied the behavior of cells in an electric field. She found that most cells will migrate, in electrophoresis, to the anode or positive pole. When she introduced rabbit spermatozoa, suspended in physiological solution at pH 7.1, into a Michaelis or Kross-Zuelzer apparatus, she observed that about one-half of the cells migrated to the anode and the other half migrated to the cathode when an electrical current was applied. Shroder then inseminated three female rabbits with three electrophoretically separated portions of spermatozoa. The one impregnated with the spermatozoa which migrated to the anode bore 6 young, all of them females. The one impregnated with the spermatozoa from the cathode bore 5 offspring, 4 males and 1 female. With the suspension of spermatozoa remaining in the middle between the two electrodes, she impregnated another female rabbit. Of the 4 young thus produced, 2 were males and 2 were females. She theorized that these results were due to the separation of the spermatozoa in the electrophoretic apparatus into two populations—one population consisting predominately of Y-bearing spermatozoa and the other of X-bearing spermatozoa. She believed that if the pH of the physiological solution were intermediate between the isoelectric points of the two populations of spermatozoa, then the two populations would exhibit opposite charges. This would appear to be verified by her observations and experiments. Shroder developed the technique and procedure to the point that it was possible to predict the sex of the offspring of rabbits with 80% accuracy (see Citation Nos. 36, 37 and 38 in Table I).

In 1935 Machowka and Schegaloff (see Citation No. 39 in Table I) attempted to duplicate Shroder's work. They observed the two-way migration of spermatozoa and inseminated female rabbits with fractions obtained by electrophoresis in the Michaelis apparatus. In 50 litters, 216 young were produced. Of these, 105 were females and 111 were males, almost the ratio which would be expected under normal breeding conditions. As a result of their work, they rejected Shroder's theory of different isoelectric points for each of the two types of sperm. They theorized that all mammalian cells possess a negative charge, and that only in adverse conditions with the lipid component of the cell membrane be destroyed and positive ions become absorbed to the cell to such an extent that the over-all, net charge of the cell will become positive. They therefore speculated that the two-way migration of the spermatozoa is due to two things. One is a passive cataphoretic movement and the other is an active negative galvanotaxis. They did not believe that the two-way migration is due to the difference in the X- and Y- chromosomes.

Kordts (see Citation No. 40 in Table I) in his experiments in 1952 on electrophoresis of rabbit spermatozoa observed a marked separation of spermatozoa. Upon subsequent insemination of the fractions in females, he obtained 127 offspring, the sex ratio being 48.4% males to 51.2% females.

Pilz (see Citation No. 41 in Table I) was working with both rabbit and bull spermatozoa. He did not have success in the two-way separation of the spermatozoa. He did observe, however, that inactive and/or dead spermatozoa may migrate to either the cathode or anode. Since he obtained no impressive separations, he did not attempt any inseminations.

Gordon (see Citation Nos. 42 and 43 in Table I) appears to have successfully separated rabbit spermatozoa by means of electrophoresis into fractions. From 201 inseminations, he obtained 31 litters and a total of 167 offspring. His accuracy in the prediction of the sex of the offspring was 71.3% for females and 63.7% for males. In the apparatus he used for electrophoresis, only one pole was accessible for extraction of spermatozoa. Therefore, it was necessary to make two trials, one with the poles reversed, in order to get the two samples of spermatozoa from both the positive and negative poles.

Gordon theorized that the migrations were due to sexual dimorphism in the spermatozoa which was the result of a difference in their surface charges. He further stated that there was no proof for electrophoretic separation due to surface charges, as Shroder observed that the temperature would affect the direction of migration.

Gordon interpreted this as follows: "At higher temperatures, the surface membranes, normally acting as electrical insulators, may lose this property and then act as conductors, so that internal particles having charges may be responsible for migration." The difference in the internal charge would be due to the differences in the X- and Y-chromosomes.

Lewin (see Citation No. 44 in Table I) observed two-directional migration of spermatozoa in an electric field in both rabbit and man. She stated that the ova of several species can be shown to migrate in an electric field and that a charged ovum could be selectively fertilized by an oppositely charged spermatozoon as particles with like charges repel and particles with unlike charges attract. The charges exhibited by the ovum and spermatozoon are a function of the pH, therefore, the pH of the medium in which fertilization takes place could favor one sex over the other. She went a step further to state that if one were to combine electrophoresis with Weir's principle (see Citation Nos. 17, 18 and 19 in Table I) then it might be possible to predict the sex of the progeny with greater accuracy than 80%.

Vesselinovitch and MacPherson (see Citation Nos. 45 and 46, respectively, in Table I) and Vesselinovitch (see Citation Nos. 47 and 48 in Table I) have done much work on the electrophoresis of bull spermatozoa. They reported that in no case did they note any two-directional movement of spermatozoa due to electrophoresis. They did observe that first, the immotile spermatozoa were carried to the anode by electrophoresis; second, that moderately active spermatozoa swim actively, after undergoing galvanotaxis, to the cathode; and third, that the highly active spermatozoa swim actively at random. In subsequent inseminations of anode- and cathode-spermatozoa, they observed no significant divergence from the normal sex ratio of the offspring. In 1960 Vesselinovitch (see Citation No. 48 in Table I) states: "In conclusion it may be said that on the basis of the previously reported work and comments made here, we believed that it is sound to state that there are no solid grounds at present on which to assume that true electrophoresis of spermatozoa may solve the problem of sex control."

Observations on Nuclear Morphology of normal human sperm by Dr. Landrum B. Shettles of Columbia-Presbyterian Medical Center in New York City (1961) finds that there are two populations of cytologically normal sperm in regard to head ad nuclear size and shape: larger, oval, and smaller, rounded types. There were no intermediate types. The smaller and rounded heads contained a centrally located chromosome, whereas the larger ones had a centrally located elongated chromosome.

Robert B. Diasio, et al., (see Citation No. 49 in Table I), studying the effects of pH upon sperm migration found that pH did not affect sperm in capillary tubes. They state that on both clinical and experimental grounds it appears unlikely that the X and Y sperm can be differentiated on the basis of migration through fluids of varying pH's.

The following U.S. patents and literature reference are also cited to exemplify the state of the prior art:
U.S. Pat. Nos. 3,687,806—Aug. 29, 1972—Van Den Bovenkamp 3,873,432—Mar. 25, 1975—Israel, et al. 3,894,529—July 15, 1975—Shrimpton 3,906,929—Sep. 23, 1975—Augspurger 3,914,168—Oct. 21, 1975—Allington 3,976,197—Aug. 24, 1976—Bhattacharya 4,007,087—Feb. 8, 1977—Ericsson
4,009,260—Feb. 22, 1977—Ericsson
Smith "Chromatographic and Electrophoretic Techniques"(1960), pages 120, 121, 123, 137.

| | | |
|---|---|---|
| 3,466,154 | Sept. 9, 1969 | Hori et al |
| 3,692,897 | Sept. 19, 1972 | Bhattacharya |
| 3,766,008 | Oct. 16, 1973 | Macomber |
| 3,973,003 | Aug. 3, 1976 | Colas |
| 4,066,537 | Jan. 3, 1978 | Barnfeld |
| 4,083,957 | Apr. 11, 1978 | Long |
| 4,085,205 | Apr. 18, 1978 | Hancock |

SUMMARY OF THE INVENTION

The invention relates to a process for separating and collecting viable female spermatozoa (X-chromosome) and male spermatozoa (Y-chromosome) of mammalian species. The apparatus for conducting the process comprises two electrically operated magnetic coils, a sterilized column or pressure tube of glass, plastic or other suitable material, joined together in the center by a ball valve, with the ends sealed by cork stoppers, or other suitable material, a DC power source, and connecting wires to the electromagnetic coils. The system is assembled so as to prevent the introduction of extraneous air into the closed pressure tube. The tube containing the semen sample may be of variable volume to accommodate semen samples of varying volume and concentration.

Accordingly, the primary object of this invention is to provide a process for separating and collecting viable female and male spermatozoa.

Another object of the invention is to provide a process for such separation and collection wherein such spermatozoa are subjected to a pressure above atmospheric acting upon the media in which they are suspended wherein such spermatozoa of varying chromatin mass will migrate without inhibition.

Still another object of the invention is to provide apparatus for a process for such separation and collection wherein such spermatozoa are contained in a tube subjected to an electrically produced longitudinal magnetic flux, thus allowing the viable female spermatozoa (X-chromosome) to accumulate at the end of the tube where magnetic flux enters and the male spermatozoa (Y-chromosome) to accumulate and concentrate at the end of the tube where magnetic flux exits.

Yet another object is to effect the separation process with positive pressure.

A further object of the invention is to provide a semen sample column or tube of variable volume, to accommodate semen samples of varying volume and concentration.

A still further object of the invention is to provide an electromagnet generating a magnetic flux of variable strength for separating and collecting viable female and male spermatozoa at the respective ends of the tube.

These together with other objects and advantages which will become subsequently apparent reside in the details of construction and operation as more fully hereinafter described and claimed, reference being had to the accompanying drawings forming a part hereof, wherein like numerals refer to like parts throughout.

BRIEF DESCRIPTION OF THE DRAWINGS

FIG. 3 is a perspective view of the coil arrangement of FIG. 2, a sample tube in which a semen sample can be maintained at a predetermined pressure and a holding block on which the tube is suspended.

FIG. 5 is a side elevational view of a plurality of hollow containers or straws for holding a semen sample.

FIG. 6 is a perspective view of a straw of FIG. 5 after separation of the contents, following which the straw can be cut as shown in FIG. 6 to retain the separate samples.

DESCRIPTION OF THE PREFERRED EMBODIMENTS

Figure 1:
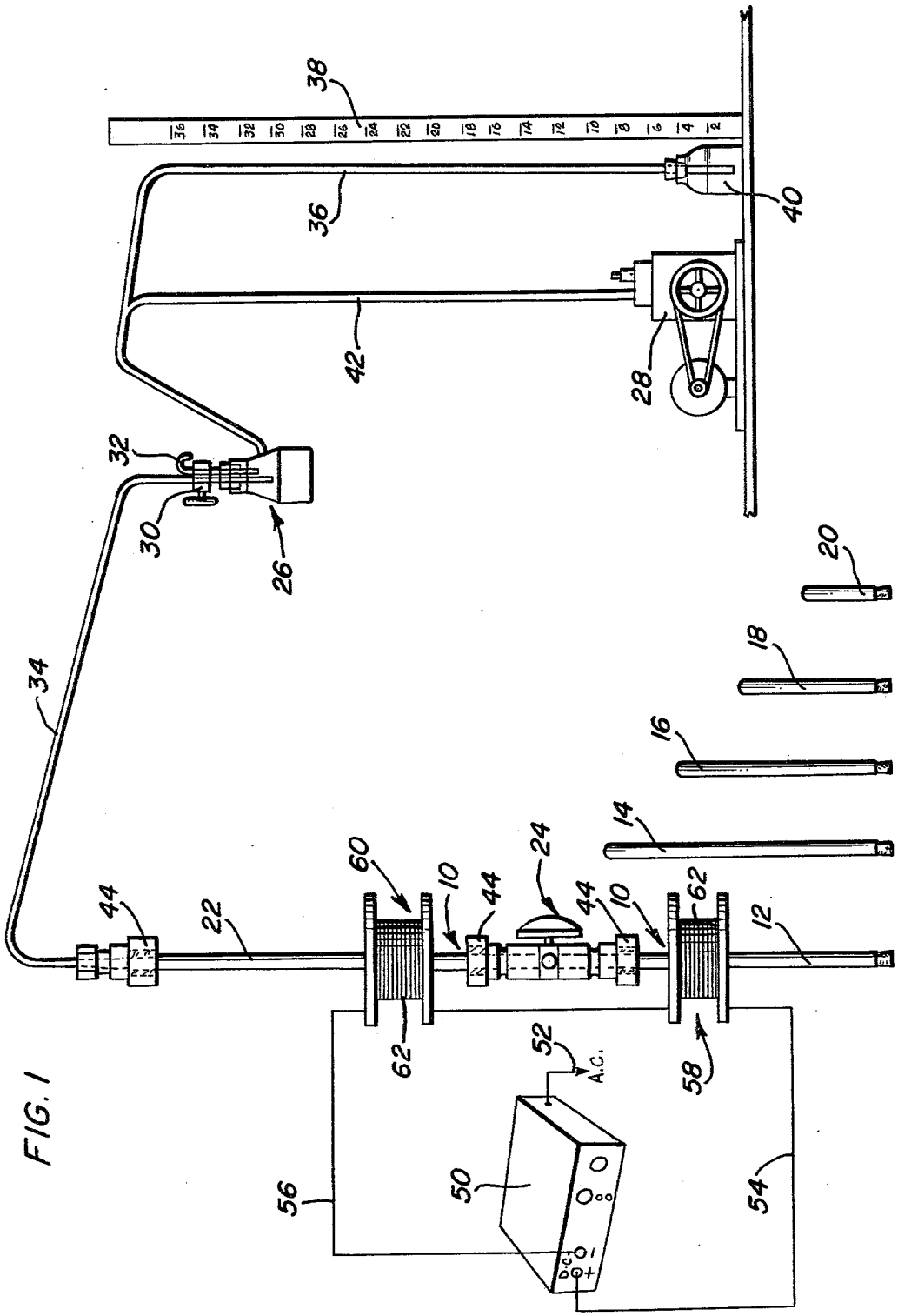
FIG. 1 is a side elevational view of the apparatus designed to separate and collect viable female spermatozoa (X-chromosome) and male spermatozoa (Y-chromosome) by subjecting the sperm sample to manometric pressure, and an electrically created magnetic flux.
Figure 2:
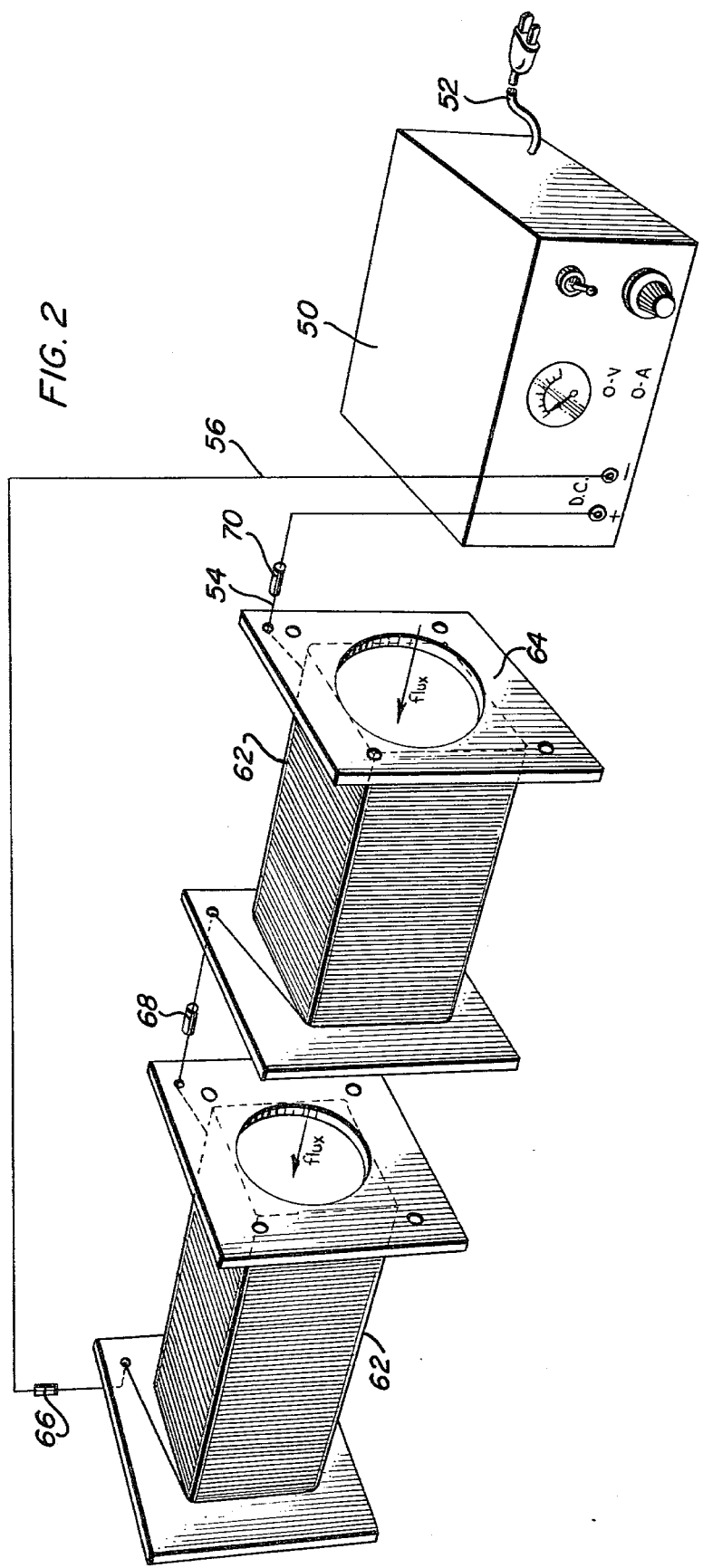
FIG. 2 is a perspective view of a pair of coils for electrically generating a longitudinal magnetic field, such as for use in the arrangement of FIG. 1. A direct current power supply for controlling the magnetic flux is also shown in association with the pair of coils connected in series.

In FIG. 1 of the drawings, there is disclosed apparatus useful in a process for separating and collecting viable female spermatozoa (X-chromosome) and male spermatozoa (Y-chromosome). A semen sample is introduced into tube 10, preferably into lower chamber 12. The volume adapters 14, 16, 18 and 20 are designed to hold volumes of 30, 50, 75 and 100 milliliters, respectively, and can be made to accommodate any typical semen sample volume. The diameter of these adapters is ¾ inch, but may be varied.

Upper chamber 22 of the column will preferably be longer than the adapter portion, in lower chamber 12, to allow for turbulence and burping, and so that an extender may be introduced in an equal volume to the semen sample in lower chamber 12.

Valve 24 of the column is a ¾ inch ball valve, thus allowing closure between lower chamber 12 and upper chamber 22.

Container 26 is a burp bottle to eliminate the possibility of fluids being drawn into vacuum pump 28, which is conventional in construction. Container 26 can be vented by valve 30 through vent tube 32 to the atmosphere. In another position of valve 30, line 34 is open to container 26, or in a third position of valve 30, both line 34 and tube 32 are closed to container 26. Manometer tube 36 and scale 38 are used to monitor the pressure during the process by measurement of the height of mercury drawn from reservoir 40 as pump 28 evacuates container 26 and tube 36 through line 42.

The entire apparatus constitutes a closed system held together by rubber percussion gaskets 44 or other suitable means, to prevent the introduction of extraneous air.

A source 50 of direct current (d.c.) is operated from power line 52, delivering direct current through line 54 and 56 to coils 58 and 60, each of which consists of a plurality of windings 62 of insulated wire wound on a support frame 64. The direction of winding of coils 58 is the same as the direction of windings of coils 60 so that the direction of the longitudinal lines of magnetic flux passing along the axis of tube 10 is from right to left in FIG. 3. Resisters 66, 68 and 70 serve to regulate the voltage drop over each coil 58 and 60 and are selected with resistance values which substantially equalize the strength of the magnetic field generated by each coil. Accordingly, the resisters can be used to compensate for dissimilarities in the coils.

Holding block 72 supports tube 10 and valve 24, and is preferably made of plastic or other suitable non-magnetic material.

Each of straws 74 in FIG. 5 is preferably a commercially available semen sample container with a capacity of about 0.5 cc of the type used in artificial insemination work and can be used in place of tube 10 and valve 24. Plugs 76 seal each end of straw 74, and are cork stoppers or other suitable material used to store a semen sample in straw 74 under a pressure greater than atmospheric pressure. This pressure is preferably generated by the reduction in internal volume of straw 74 as the second plug 76 is inserted thereinto, thereby compressing the contents of straw 74 and creating the desired pressure. In FIG. 6, one of straws 74 has undergone separation of spermatozoa contents according to the process to be hereinafter described, and has been removed from between coils 58 and 60. Straw 74 is then cut centrally to leave portions 78 and 80, each of which contains samples of separated spermatozoa as shown in FIG. 6.

The general procedure for the operation is as follows: a semen sample is introduced between coils 58 and 60 in the following manner. First, straw 74 is plugged (best seen in FIG. 5) by stopper 76. Straw 74 is completely filled with the semen sample in its appropriate commercial extender and, when filled, another stopper 76 is inserted to leave a slight pressure on the sample. This apparatus is then placed between coils 58 and 60, as shown in FIG. 3, at the appropriate distance between coil 58 and coil 60. Then the appropriate magnetic force is applied to straw 74 by activating a direct current power supply 50 deliver direct current to coils 58 and 60. After separation has occurred, straw 74 is removed from block 72, and straw 74 is broken to retain the separated fractions in portions 78 and 80 as shown in FIG. 6.

Figure 4:
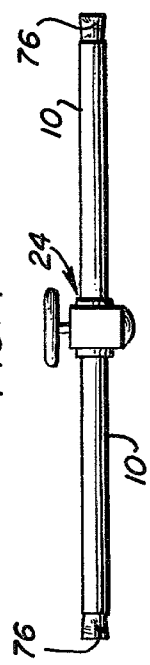
FIG. 4 is a side elevational view of a sample holder tube in which a semen sample is placed prior to being exposed to the aforementioned separation process.

Samples in other containers containing male spermatozoa may be separated in a similar or like manner, such as by separation in the apparatus of FIG. 1, where the sample is contained in tube 10 and connected to a device for applying vacuum during magnetic separation of the sample. Under this procedure of operation under vacuum, a semen sample is introduced into tube 10, as best seen on FIGS. 1 and 4. Valve 24 is then closed, and the column is then subjected to a manometric pressure of approximately 12 inches of mercury, and valve 24 is gently opened. The system is subjected to this vacuum until column turbulence ceases. Negative pressure is then increased to the maximum, approximately 30 inches of mercury, for about one hour, with variations in maximum pressure and time length selected according to the physiology of the semen, and atmospheric conditions. A magnetic field is generated by coils 58 and 60 by introducing current from d.c. power supply 50, and when the desired separation has occurred, valve 24 is closed to prevent mixing of the separated female and male spermatozoa. Valve 24 preferably contains a ¾ inch ball valve which allows closure between the lower portion and upper portion of tube 10. Container 26 is a burp bottle which eliminates the possibility of fluid being drawn into vacuum pump 28 or manometer tube 36. Manometer tube 36, scale 38, and reservoir 40 are used for monitoring the pressure in the system during the separation process. The entire system is held in a airtight configuration with the aid of rubber percussion gaskets 44 or other suitable means, preventing the introduction of extraneous air.

Since the present invention can be practiced in the manner taught herein without regard to the explanation of the theory and principles responsible for effects taught, the explanations advanced herein are intended in no way to limit the scope of the present invention defined by the claims.

Cellular respiration may be defined as the osmotic chemical process or processes by which a plant or animal absorbs oxygen and gives off the products formed by the oxidation in the tissues.

Spermatozoa carry on cellular respiration and our work demonstrates that there are substantial differences in the amounts of oxygen consumed between the X- and Y- spermatozoa populations. Oxygen consumption is related to the separation of the X- and Y- spermatozoa due to their respiration.

The present invention apparatus is a closed system and the positive pressures applied to this system, however slight, changes the osmotic pressures within the system and allows an even flow of spermatozoa to migrate due to the difference in the molecular weight of the chromatin mass within the X- and Y- spermatozoa.

By definition, a semen sample contains spermatozoa of the X and Y- types, glandular fluids and other reproductive organ fluids from the male of the species. The extender is any commercial extender used in artificial insemination work of that particular species.

X- and Y- mammalian spermatozoa have not been separated, to any degree, due to their size variations. Also, they have not been separated to any degree by different weights of the two. This is due to their infinitesimally small differences both in weight and size. These variations cannot be detected under the ordinary light microscope. However, these variations can be detected by the use of the electron microscope, as well as phase contrast microscope. We have done this with the electron microscope and the literature bears out these size variations in chromatin mass of the X- and Y-mammalian spermatozoa.

By changing the osmotic pressures within the closed system, as previously mentioned, it is possible to utilize the difference in size and weight of the X- and Y- spermatozoa in the separation procedure. Utilizing this force the present invention has enhanced the separation of the X- and Y- spermatozoa as shown in the apparatus in FIGS. 1 and 3.

The electro-potential energy differences between the X- and Y-mammalian spermatozoa are explained by relating them to the maturation process of the animal germ cell.

In spermatogenesis, the X- and Y- spermatids are formed during meiosis, a special division of the animal germ cells. Somatic cell division within the body takes place due to a phenomenon known as mitosis. Germ cell division takes place similar to mitosis, but an additional stage called meiosis allows for the production and maturation of the sperm and egg to be developed. This cell division is accomplished by the centromeres (poles) within a cell dividing and form at each end of the cell. They go through a process that separates the chromatin mass into equal parts, forming a new cell, and the process repeats as new cells are formed. The centromeres act as positive and negative poles, separating the chromatin mass equally at the two ends. In the case of the spermatozoa, the second metaphase shows the two spermatids, one being positive and the other negative. Thus, we have two spermatids carrying a positive (+) charge and two carrying a negative (−) charge. Two are X-spermatids and two are Y-spermatids, and upon maturation, will be mature X- and Y- spermatozoa.

In the case of the egg (ova) the Y-polar body is thrown off and never matures or develops. Only the X-polar body of one is retained with the egg. Thus, the egg always carries the X-chromatin material.

During fertilization, this electro-potential energy of the sperm is neutralized due to the hundreds of sperm, both X- and Y-, which bombard the egg in an attempt to unite with it in the fertilization process. This sets up a chemical neutralizing reaction around the egg, allowing only one of the spermatozoa to ultimately unite with the ova, regardless of the electro-potential of the spermatozoa. Without this bombardment and chemical reaction around the egg, no fertilization would take place. The present invention utilizes this electro-potential energy of the spermatozoa in the separation process of X- and Y- mammalian spermatozoa.

Spermatozoa of the X- and Y- types with different electro-potential energy are attracted to their opposite charge. In the case of the X-types of spermatozoa, they are negative (−) in polarity, therefore they will migrate and toward the positive (+) pole, whereas the Y-spermatozoa are of positive polarity and will migrate with the current flow opposite to their charge.

It needs to be stated that in the case of some animals within a given species, their spermatozoa separate more distinctly into two populations depending upon the intensity of the magnetic force applied. An explanation for this lies in the fact that the pH of the semen sample collected from the animal has an influence upon the positive and negative ions incorporated within the spermatozoa themselves. This is an important aspect as to why the magnetic forces influence and cause the separation of the X- and Y-spermatozoa in the present invention. It should be noted that pH is the measurement of the hydrogen ion concentration that causes current to flow within an electrolyte system. Also, when the pH of a semen sample is neutral (pH 7), the spermatozoa carry a positive and negative influencing charge that allows migration to their respective opposite pole from their innate charge.

The present invention for the separation of viable X- and Y-spermatozoa utilizes commercial extenders. These extenders are commonly used in artificial breeding of animals within a species. This allows for a practical method to handle semen samples as well as separation of the X- and Y-spermatozoa.

One population of spermatozoa is acidophilic (acid-loving spermatozoa) and the other population is basophilic (base loving spermatozoa). Samples from each population are subjected to acid and basic solutions to determine the types of spermatozoa they contain.

Populations from each sample, taken from the X- and Y-spermatozoa of the invention are subjected to a system that will measure particle sizes from 0.5 microns and larger. It will measure their diameter, length and/or width, and will allow a count of the total number. In this manner, slight variations in the size of the spermatozoa may be detected. The X-spermatozoa is slightly wider than the Y-spermatozoa.

Preferably, direct current power supply 50 produces a direct current output having a potential adjustable through the range of 0 to 25 volts, and can deliver a current of from 0 to 2 amperes. When conventional coils 58 and 60 are employed, operation within these parameters is sufficient to effect separation within a reasonable time.

The foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as new is as follows:

1. A process for separating and collecting viable female spermatozoa (X-chromosome) and male spermatozoa (Y-chromosome) in a semen sample, which process comprises subjecting the semen sample to a magnetic field to cause the female (X-chromosome) and male (Y-chromosome) spermatozoa to migrate in opposite directions along the direction of said magnetic field.

2. The process of claim 1 wherein said sample is contained in an elongated tube having closed ends, said tube being aligned in the direction of the magnetic field, wherein said female (X-chromosome) spermatozoa are collected at the end of said tube at which the magnetic flux of the magnetic field enters, and said male (Y-chromosome) spermatozoa are collected at the opposite end of said tube, at which magnetic flux exits.

3. The process of claim 2 wherein said semen sample is subjected to a pressure above atmospheric pressure, whereby non-cohesive migration of said female and male spermatozoa occurs.

4. The process of claim 2 wherein said sample includes an extender, said female spermatozoa, male spermatozoa, said extender constituting a liquid medium, wherein the osmotic pressure of said liquid medium is changed to facilitate separation and collecting of the female spermatozoa and male spermatozoa.

5. The process of claim 2 wherein said magnetic field is generated by a pair of coils disposed along the length of said tube, each tube having an axis substantially coincident with said tube, wherein said process comprises applying a direct electrical current to each of said coils, wherein the coils are oriented in the same direction; and each coil generates a magnetic field acting in the same direction along the longitudinal axis of said tube.

6. The process of claim 5 wherein said direct electrical current is applied at a controllably varying voltage and amperage, whereby the magnetic field applied to the sample is varied.

7. The process of claim 2 wherein said tube comprises a straw sealable at each end, and said process comprises placing said semen sample mixed with semen extender material in said straw, sealing the ends of said tube, placing the straw along the direction of a magnetic field until separation of said male spermatozoa and female spermatozoa is substantially complete, and cutting said straw centrally to effect separation of the female and male spermatozoa.

8. The process of claim 7 wherein said straw is subjected to a pressure above atmospheric pressure, whereby separating of female spermatozoa from male spermatozoa is increased and facilitated.

9. The method of claim 2 wherein said tube is provided with valve means centrally disposed along said tube, and said valve means is closed after said female spermatozoa have separated from said male spermatozoa, whereby said valve means prevents mixing of separated female and male spermatozoa and enables collecting thereof in said tube.

10. The process of claim 1 wherein said process comprises subjecting the semen sample to negative pressure to assist in separation thereof.

11. The process of claim 10 wherein said negative pressure is equivalent to manometric pressure of about 30 inches of mercury.

12. The process of claim 11 wherein the negative pressure is applied to the sample for approximately one hour.

* * * * *